US012714514B2

(12) United States Patent
Stanton et al.

(10) Patent No.: US 12,714,514 B2
(45) Date of Patent: Aug. 25, 2026

(54) MULTI-STAGE DILATOR AND CANNULA SYSTEM AND METHOD

(71) Applicant: Stryker Corporation, Portage, MI (US)

(72) Inventors: Russell Stanton, Lunenberg, MA (US); Scott Coppen, Amesbury, MA (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/820,781

(22) Filed: Aug. 30, 2024

(65) Prior Publication Data

US 2024/0415583 A1 Dec. 19, 2024

Related U.S. Application Data

(63) Continuation of application No. 17/990,857, filed on Nov. 21, 2022, now Pat. No. 12,102,394, which is a
(Continued)

(51) Int. Cl.
*A61B 17/02* (2006.01)
*A61B 17/34* (2006.01)
(Continued)

(52) U.S. Cl.
CPC .......... *A61B 34/20* (2016.02); *A61B 17/0218* (2013.01); *A61B 17/025* (2013.01); *A61B 17/34* (2013.01); *A61B 17/3421* (2013.01); *A61B 90/39* (2016.02); *A61B 2017/0256* (2013.01); *A61B 17/3403* (2013.01); *A61B 2034/2055* (2016.02); *A61B 2034/2059* (2016.02); *A61B 2034/2065* (2016.02); *A61B 2034/2074* (2016.02); *A61B 34/30* (2016.02); *A61B 2090/3762* (2016.02);
(Continued)

(58) Field of Classification Search
CPC ......... A61B 34/20; A61B 34/30; A61B 17/02; A61B 17/0218; A61B 17/34; A61B 17/3421; A61B 17/3433; A61B 17/3435
USPC .................................................. 600/201–246
See application file for complete search history.

(56) References Cited

U.S. PATENT DOCUMENTS

| | | | |
|---|---|---|---|
| 4,994,027 | A | 2/1991 | Farrell |
| 5,799,055 | A | 8/1998 | Peshkin et al. |

(Continued)

FOREIGN PATENT DOCUMENTS

| | | | |
|---|---|---|---|
| CN | 101589964 | A | 12/2009 |
| CN | 201422918 | Y | 3/2010 |

(Continued)

OTHER PUBLICATIONS

English language abstract and machine-assisted English translation for CN 101579269 extracted from espacenet.com database on Jan. 9, 2020, 8 pages.

(Continued)

*Primary Examiner* — Eduardo C Robert
*Assistant Examiner* — Christina NegrelliRodriguez
(74) *Attorney, Agent, or Firm* — Howard & Howard Attorneys PLLC

(57) ABSTRACT

A multi-stage dilator and cannula assembly for use in surgical procedures, including minimally invasive surgical procedures, to provide tissue dilation and opening of a portal to enable the surgeon to access and provide treatment to anatomical feature of interest.

15 Claims, 13 Drawing Sheets

Related U.S. Application Data continuation of application No. 16/884,492, filed on May 27, 2020, now Pat. No. 11,534,244, which is a continuation of application No. 15/646,631, filed on Jul. 11, 2017, now Pat. No. 10,695,133.

(60) Provisional application No. 62/412,450, filed on Oct. 25, 2016, provisional application No. 62/361,040, filed on Jul. 12, 2016.

(51) Int. Cl.
*A61B 34/20* (2016.01)
*A61B 90/00* (2016.01)
*A61B 34/30* (2016.01)
*A61M 29/00* (2006.01)

(52) U.S. Cl.
CPC ................. *A61B 2090/3945* (2016.02); *A61B 2090/3979* (2016.02); *A61B 2090/3983* (2016.02); *A61M 29/00* (2013.01)

(56) References Cited

U.S. PATENT DOCUMENTS 5,921,992 A 7/1999 Costales et al.
6,149,592 A 11/2000 Yanof et al.
6,236,875 B1 5/2001 Bucholz et al.
6,275,725 B1 8/2001 Cosman
6,533,455 B2 3/2003 Graumann et al.
6,772,002 B2 8/2004 Schmidt et al.
6,785,572 B2 8/2004 Yanof et al.
7,194,120 B2 3/2007 Wicker et al.
7,251,522 B2 7/2007 Essenreiter et al.
7,587,235 B2 9/2009 Wist et al.
7,699,877 B2 4/2010 Davison
7,722,530 B2 5/2010 Davison
7,799,036 B2 9/2010 Davison et al.
8,016,835 B2 9/2011 Birkmeyer et al.
8,046,054 B2 10/2011 Kim et al.
8,126,114 B2 2/2012 Naylor et al.
8,394,144 B2 3/2013 Zehavi et al.
8,454,583 B2 6/2013 Perez-Cruet et al.
8,454,620 B2 6/2013 Ralph et al.
8,457,790 B2 6/2013 Blondel et al.
8,509,503 B2 8/2013 Nahum et al.
8,535,336 B2 9/2013 Trovato
8,740,912 B2 6/2014 Stark
8,761,337 B2 6/2014 Naylor et al.
8,795,188 B2 8/2014 Maschke
8,974,460 B2 3/2015 De la Fuente Klein et al.
9,125,680 B2 9/2015 Kostrzewski et al.
9,237,861 B2 1/2016 Nahum et al.
9,283,048 B2 3/2016 Kostrzewski et al.
9,308,050 B2 4/2016 Kostrzewski et al.
9,545,233 B2 1/2017 Sirpad et al.
9,550,299 B2 1/2017 Wolf et al.
9,750,432 B2 9/2017 Nahum et al.
9,814,535 B2 11/2017 Bar et al.
9,833,292 B2 12/2017 Kostrzewski et al.
10,004,562 B2 6/2018 Kostrzewski et al.
10,039,476 B2 8/2018 Nahum et al.
10,076,385 B2 9/2018 Shoham et al.
10,136,952 B2 11/2018 Couture et al.
10,159,534 B2 12/2018 Maillet et al.
10,695,133 B2* 6/2020 Stanton ................ A61B 17/025
10,744,004 B2 8/2020 Lopez et al.
11,110,297 B2 9/2021 Lamoureux et al.
11,534,244 B2* 12/2022 Stanton ................ A61B 17/025
12,102,394 B2* 10/2024 Stanton ............. A61B 17/3421
2006/0004398 A1 1/2006 Binder et al.
2007/0066887 A1 3/2007 Mire et al.
2007/0156157 A1 7/2007 Nahum et al.
2007/0255305 A1 11/2007 McMichael et al.
2008/0058861 A1 3/2008 Cooper et al.
2009/0088773 A1 4/2009 Zhao et al.
2009/0149857 A1 6/2009 Culbert et al.
2011/0201887 A1 8/2011 Greenblatt et al.
2012/0232552 A1 9/2012 Morgenstern Lopez et al.
2012/0253135 A1 10/2012 Simonson
2014/0249546 A1 9/2014 Shvartsberg et al.
2014/0277204 A1* 9/2014 Sandhu .................. A61F 2/447 606/86 A
2015/0196365 A1 7/2015 Kostrzewski et al.
2015/0202009 A1 7/2015 Nussbaumer et al.
2015/0366624 A1 12/2015 Kostrzewski et al.
2016/0030117 A1 2/2016 Mewes
2016/0081754 A1 3/2016 Kostrzewski et al.
2016/0174914 A1 6/2016 Lerch et al.
2016/0220320 A1 8/2016 Crawford et al.
2016/0235492 A1 8/2016 Morard et al.
2016/0278875 A1 9/2016 Crawford et al.
2017/0000579 A1* 1/2017 Mark ................ A61B 17/3417
2017/0071691 A1 3/2017 Crawford et al.
2017/0079727 A1 3/2017 Crawford et al.
2017/0172669 A1 6/2017 Berkowitz et al.
2017/0231702 A1 8/2017 Crawford et al.
2017/0239002 A1 8/2017 Crawford et al.
2017/0239003 A1 8/2017 Crawford et al.
2017/0239006 A1 8/2017 Crawford et al.
2017/0245951 A1 8/2017 Crawford et al.
2017/0252112 A1 9/2017 Crawford et al.
2017/0258533 A1 9/2017 Crawford et al.
2017/0258535 A1 9/2017 Crawford et al.
2017/0312039 A1 11/2017 Crawford et al.
2017/0348061 A1 12/2017 Joshi et al.
2017/0360513 A1 12/2017 Amiot et al.
2017/0360517 A1 12/2017 Crawford et al.
2018/0000546 A1 1/2018 Crawford et al.
2018/0110573 A1 4/2018 Kostrzewski
2018/0116739 A1 5/2018 Gogarty et al.
2018/0116740 A1 5/2018 Gogarty et al.
2018/0125597 A1 5/2018 Gogarty et al.
2018/0157238 A1 6/2018 Gogarty et al.
2018/0221098 A1 8/2018 Forsyth et al.
2018/0235715 A1 8/2018 Amiot et al.
2018/0250077 A1 9/2018 Xu et al.
2018/0256259 A1 9/2018 Crawford
2018/0271605 A1 9/2018 Kostrzewski et al.
2018/0346008 A1 12/2018 Nahum et al.
2019/0000561 A1 1/2019 Decker et al.
2019/0000569 A1 1/2019 Crawford et al.
2019/0021795 A1 1/2019 Crawford et al.
2019/0021799 A1 1/2019 Crawford et al.
2019/0021800 A1 1/2019 Crawford et al.
2019/0029759 A1 1/2019 Mcdonell
2019/0029765 A1 1/2019 Crawford et al.
2019/0038362 A1 2/2019 Nash et al.
2019/0053859 A1 2/2019 Couture et al.
2019/0069961 A1 3/2019 Smith et al.
2019/0099222 A1 4/2019 Nahum et al.
2019/0117313 A1 4/2019 Crawford
2019/0239964 A1 8/2019 LeBoeuf et al.
2019/0269467 A1 9/2019 Forsyth et al.
2019/0274765 A1 9/2019 Crawford et al.
2020/0281664 A1 9/2020 Stanton et al.
2023/0088321 A1 3/2023 Stanton et al.

FOREIGN PATENT DOCUMENTS

CN 201542641 U 8/2010
CN 101700184 B 1/2011
CN 101579269 B 4/2011
CN 102300512 A 12/2011
CN 202146362 U 2/2012
CN 101853333 B 11/2012
CN 103181811 A 7/2013
CN 103533904 A 1/2014
CN 103732132 A 4/2014
CN 103957984 A 7/2014
EP 0935974 B1 10/2003
WO 2006017507 A2 2/2006
WO 2012173697 A1 12/2012
WO 2015115809 A1 8/2015

(56) References Cited

FOREIGN PATENT DOCUMENTS

| | | | |
|---|---|---|---|
| WO | 2017036340 | A1 | 3/2017 |
| WO | 2017122202 | A1 | 7/2017 |
| WO | 2018185729 | A1 | 10/2018 |

OTHER PUBLICATIONS

English language abstract and machine-assisted English translation for CN 101700184 extracted from espacenet.com database on Jan. 9, 2020, 10 pages.
English language abstract and machine-assisted English translation for CN 101853333 extracted from espacenet.com database on Jan. 9, 2020, 9 pages.
English language abstract and machine-assisted English translation for CN 103181811 A extracted from espacenet.com database on Jun. 3, 2021, 15 pages.
English language abstract and machine-assisted English translation for CN 201422918 extracted from espacenet.com database on Jan. 9, 2020, 7 pages.
English language abstract and machine-assisted English translation for CN 201542641 extracted from espacenet.com database on Jan. 9, 2020, 10 pages.
English language abstract and machine-assisted English translation for CN 202146362 U extracted from espacenet.com database on Jun. 3, 2021, 8 pages.
English language abstract and machine-assisted English translation for WO 2015/115809 extracted from espacenet.com database on Jan. 9, 2020, 8 pages.
English language abstract for CN 101589964 A extracted from espacenet.com database on Jun. 3, 2021, 2 pages.
English language abstract for CN 103533904 A extracted from espacenet.com database on Jun. 3, 2021, 2 pages.
English language abstract for CN 103732132 A extracted from espacenet.com database on Feb. 2, 2022, 2 pages.
English language abstract for CN 103957984 A extracted from espacenet.com database on Feb. 2, 2022, 2 pages.
English language abstract for WO 2017/036340 extracted from espacenet.com database on Jan. 9, 2020, 2 pages.
International Search Report from the Korean Patent Office in International Application No. PCT/US2017/041493 dated Oct. 20, 2017.
Pal jug, Eric et al. "The JPL Serpentine Robot: a 12 DOF System for Inspection", NASA JPL Technical Reports Server, https://trs.jpl.nasa.gov/handle/2014/29159, Jan. 1, 1995, 5 pages.
Written Opinion of the International Searching Authority from the Korean Patent Office in International Application No. PCT/US2017/041493 dated Oct. 20, 2017.
English language abstract for CN 102300512 A extracted from espacenet.com database on Feb. 27, 2024, 2 pages.

* cited by examiner

MULTI-STAGE DILATOR AND CANNULA SYSTEM AND METHOD

CROSS-REFERENCE TO RELATED APPLICATIONS

This application is a Continuation of U.S. patent application Ser. No. 17/990,857, filed on Nov. 21, 2022, which is a Continuation of U.S. patent application Ser. No. 16/884,492, filed on May 27, 2020, now issued as U.S. Pat. No. 11,534,244 on Dec. 27, 2022, which is a Continuation of U.S. patent application Ser. No. 15/646,631, filed on Jul. 11, 2017 and issued as U.S. Pat. No. 10,695,133 on Jun. 30, 2020, which claims the benefit of priority of U.S. Provisional Application No. 62/361,040, filed Jul. 12, 2016, and U.S. Provisional Application No. 62/412,450, filed Oct. 25, 2016, the entire teachings of which are each incorporated by reference in their entirety.

BACKGROUND

Surgical procedures, such as minimally-invasive procedures, may require a surgeon to insert surgical tools inside the body of the patient to a particular depth to reach the target area inside the patient's body. For example, minimally invasive spinal surgical procedures have been used for stabilization of vertebral bones and spinal joints and for relieving of pressure applied to the spinal nerves. Such procedures may utilize relatively small incisions and insertion of tubular retractors and cannulas while minimizing damage to muscles and other surrounding anatomical features. Minimally invasive surgical approaches can be faster, safer and require less recovery time than conventional open surgeries. There is a continuing need for improvement to the safety and speed of surgical procedures, such as minimally-invasive surgical procedures.

SUMMARY

Various embodiments include a multi-stage dilator and cannula assembly for use in surgical procedures, including minimally invasive surgical procedures, to provide tissue dilation and opening of a portal to enable the surgeon to access and provide treatment to anatomical feature of interest.

Embodiments include a multi-stage dilator and cannula assembly that includes a plurality of elongated members in a nested configuration that are slidable relative to one another along a central axis, each member having a length dimension between a head end and a tip end of the member, and each successive member of the plurality of members extending radially outward from a central member has a larger outer dimension and a shorter length dimension than the preceding member.

In various embodiments, the plurality of elongated members is configured such that an application of a force in a first direction on the head end of a first member causes the first member and any members of the assembly located radially outward of the first member to move in the first direction, such as into the body of a patient. The first member and any members located radially outward of the first member may be moved in the first direction relative to any members of the assembly located radially inward of the first member. In embodiments, the application of a force on the first member in a second direction opposite the first direction causes the first member to move in the second direction relative to any members of the assembly located radially outward of the first member.

Further embodiments include methods of performing a surgical procedure using a multi-stage dilator and cannula assembly. Further embodiments include systems for performing robotically-assisted image-guided surgery using a multi-stage dilator and cannula assembly.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Figure 1A:
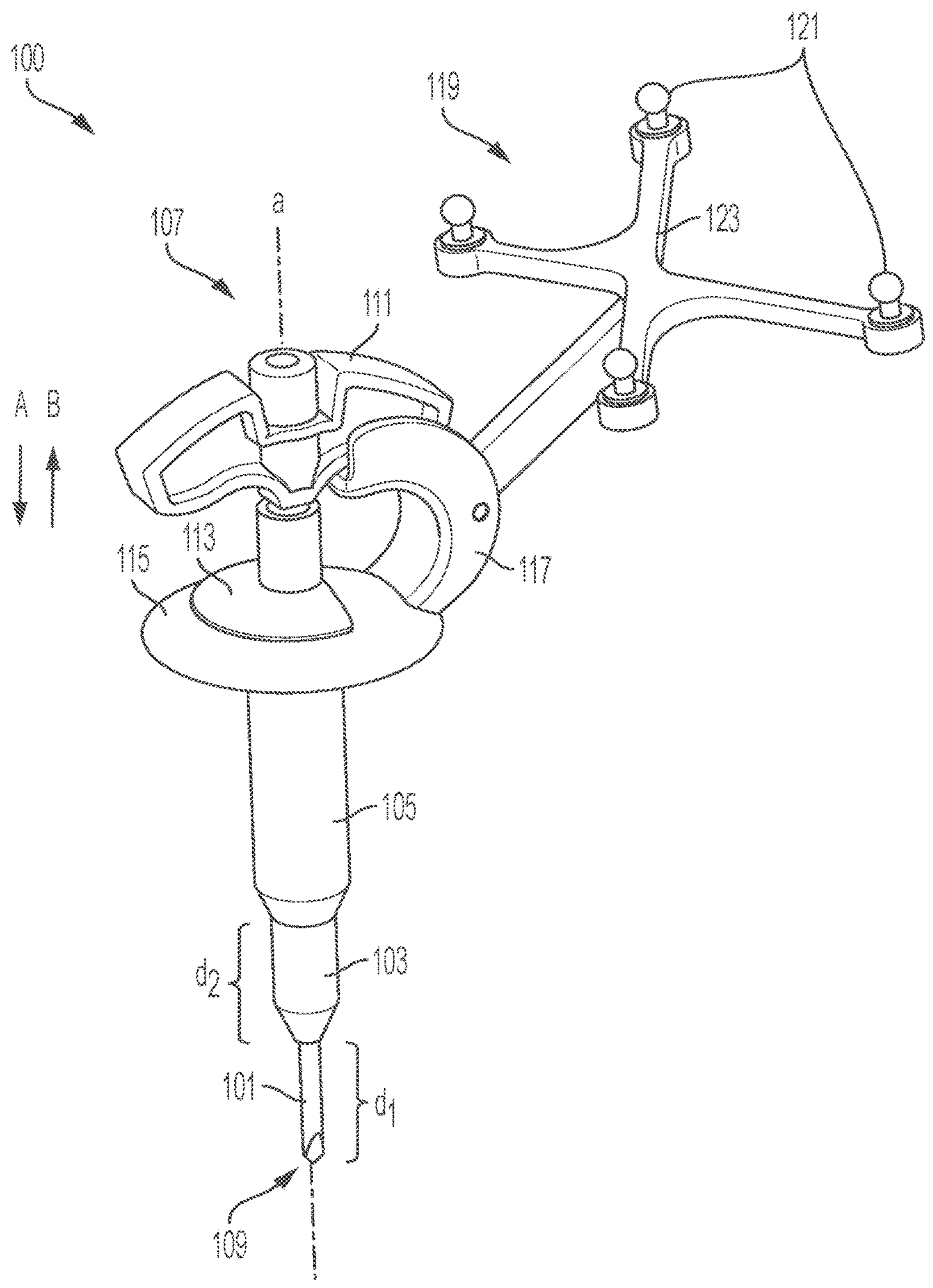
FIGS. 1A-1B are perspective views of a dilator and cannula assembly according to one embodiment.
Figure 1B:
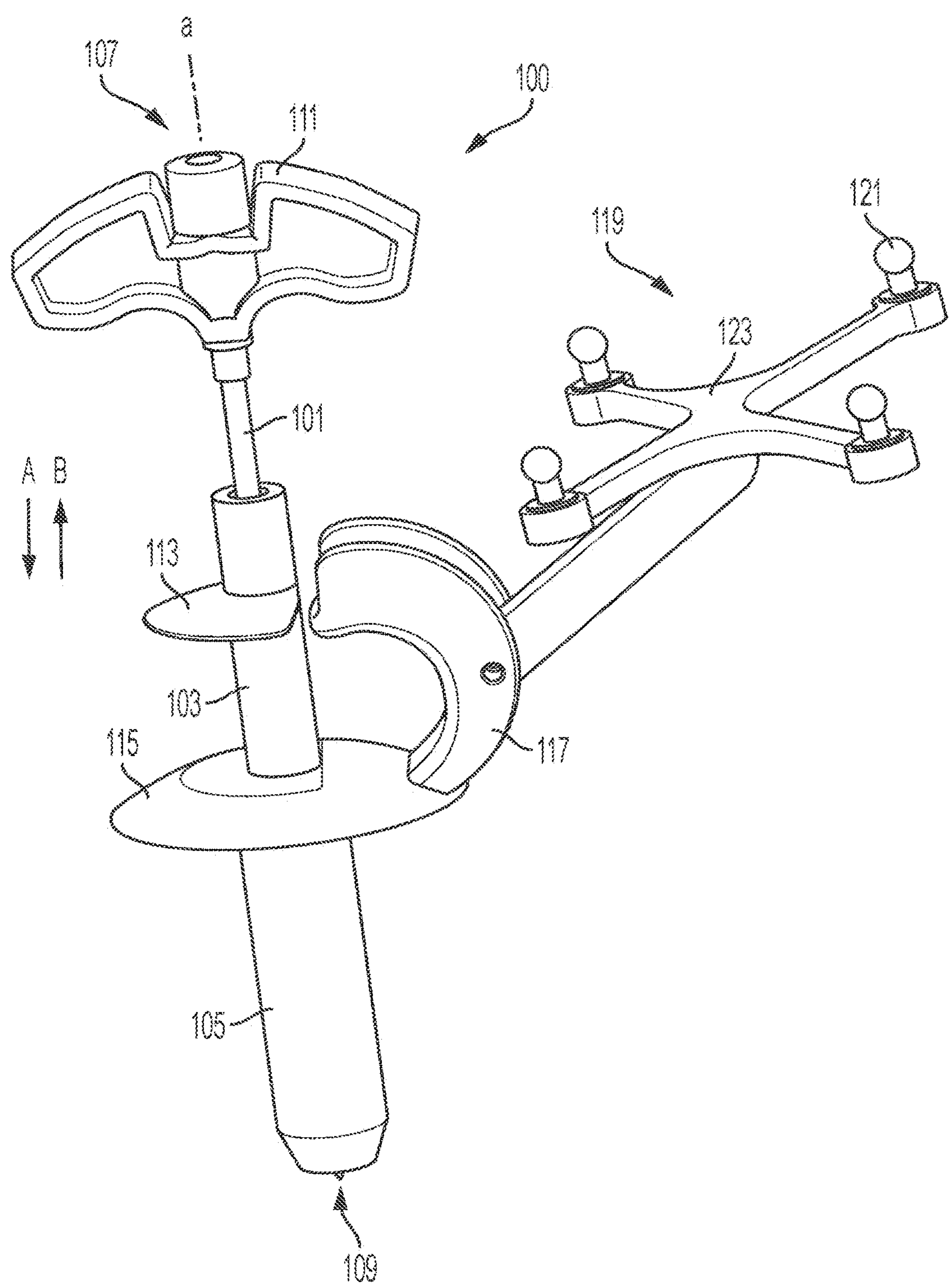

An embodiment of a multi-stage dilator and cannula assembly 100 is illustrated in FIGS. 1A and 1B. The assembly 100 includes a plurality of elongated members 101, 103, 105 in a nested configuration such that the members 101, 103 and 105 may slide relative to one another along a longitudinal axis, a. The first member 101 may have either a hollow or solid interior and may comprise a needle, a cannula or a similar elongated structure. The second member 103 may comprise a cannula having a central opening extending lengthwise through the second member 103 and sized and shaped to receive the first member 101 in sliding engagement. The third member 105 may also comprise a cannula having a central opening extending lengthwise through the third member 105 and sized and shaped to receive the second member 101 in sliding engagement.

Each of the members 101, 103 and 105 has a length extending between a first end (i.e., a head end 107) and a second end (i.e., a tip end 109) of the member. Proximate to the head end 107 of each of the members may be one or more features, such as a handle, knob, flange, etc., that may enable a user to easily grip and manipulate the members. The lengths of the members 101, 103 and 105 may vary, such that the length of the first member 101 may be greater than the length of the second member 103, and the length of the second member 103 may be greater than the length of the third member 105. FIG. 1A illustrates the assembly 100 with the head ends 107 of the members 101, 103 and 105 positioned adjacent to one another. In this configuration, the tip end 109 of the first member 101 extends beyond the tip end 109 of the second member 103 by a distance, $d_1$, and the tip end 109 of the second member 103 extends beyond the tip end 109 of the third member 105 by a distance, $d_2$. FIG. 1B illustrates the assembly 100 in a different configuration where the tip ends 109 of the members 101, 103 and 105 are substantially coincident with one another and the head ends 107 of the members 101, 103 and 105 are spaced apart.

A multi-stage dilator and cannula assembly 100 according to various embodiments may include a plurality of nested tubular or hollow members (e.g., cannulas) around a central (e.g., pilot) member, where extending radially outward from the central member, each successive member may have a relatively larger outer dimension (i.e., diameter) and a relatively shorter length dimension. In one non-limiting example, the first or central member 101 may have an outer diameter of approximately 4 mm (e.g., 2-5 mm), the second member 103 which surrounds the first member 101 may have an inner diameter of approximately 4 mm (e.g., 2-5 mm) and an outer diameter of approximately 9 mm (e.g., 7-10 mm), and the third member 105 which surrounds the second member 103 may have an inner diameter of approximately 9 mm (e.g., 7-10 mm) and an outer diameter of approximately 12 mm (e.g., 11-15 mm). When the assembly 100 is configured as shown in FIG. 1A, the tip end 109 of the first or central member 101 may extend beyond the tip end 109 of the second member 103 by a distance of approximately 25 mm (e.g., 10-40 mm) and the tip end 109 of the second member 103 may extend beyond the tip end 109 of the third member 105 by a distance of approximately 25 mm (e.g., 10-40 mm). The assembly 100 as a whole may be relatively rigid, with the larger-diameter and relatively stiffer outer cannula members 103 and 105 surrounding and supporting the smaller-diameter central (e.g., pilot) member 101 over a large portion of its length (e.g., >50%, such as 75-90%) when the assembly 100 is in the configuration shown in FIG. 1A.

As discussed above, each of the members 101, 103 and 105 may include a feature such as a handle, knob, flange, etc., which may be located proximate the head end 107 of the member that may enable a user to easily grip and manipulate the members, such as by applying a downward force on a member in the direction of arrow A, or an upward force on a member in the direction of arrow B. In the exemplary embodiment of FIGS. 1A-1B, the first member 101 includes a handle 111 at the head end 107, and the second member 103 includes a flange 113 at the head end 107 that extends transverse to the length dimension of the member 103, and the third member 105 also includes a flange 115 at the head end 107 that extends transverse to the length dimension of the member 105. In this embodiment, the third member 105 also includes a c-shaped protrusion 117 that extends from flange 115 in the direction of the handle 111 of the first member 101 and which may facilitate grasping and holding of the entire assembly 100 by a user.

At least some of the members in the assembly 100 may include one or more features that are configured to "capture" one or more members located radially outward from that member in the nested assembly 100, such that when a particular member having such a feature is pushed in a first direction (e.g., a force is applied to the member in the direction of arrow A in FIG. 1A), the member being pushed also pushes on the one or more members of the nested assembly 100 located radially-outward from the member being pushed, causing the member being pushed and the member(s) located radially-outward from that member to move together in the direction of the applied force. Any member(s) located radially inward from the member being pushed may not be similarly "captured," and thus may not move together with the member being pushed in the direction of the applied force.

In the embodiment shown in FIG. 1A, for example, the handle 111 of the first member 101 is larger than the opening in the second member 103 in a direction transverse to the length dimension of the second member 103, so that when first member 101 is pushed in the direction of arrow A, the handle 111 of the first member 101 pushes down on and captures the second member 103, thereby causing the second member 103 to advance in the direction of arrow A in conjunction with the first member 101. Similarly, the flange 113 of the second member 103 is dimensioned larger than the opening in the third member 105 so that when the second member 103 is pushed in the direction of arrow A (i.e., either by the second member 103 being directly pushed or by it being "captured" by the advancement of the first member 101), the flange 113 of the second member 103 pushes down on an captures the third member 105, thereby causing the third member to advance in the direction of arrow A in conjunction with the second member 103.

It is noted that in this embodiment, advancing a member in the direction of arrow A does not result in the member pushing down on and "capturing" any member that is located radially-inward from the member being pushed in the nested assembly 100. For example, when the third member 105 is advanced in the direction of arrow A, such as by a user directly applying a force to the flange 115 of the third member 105, the third member 105 may freely slide in the direction of arrow A relative to the first and second members 101, 103, which are located radially-inward from the third member 105. Similarly, applying a direct force in the direction of arrow A to the flange 113 of the second member 103 will "capture" the third member 105 (which is located radially-outward from the second member 103) but does not capture the first member 101 (which is located radially-inward from the second member 103). Thus, the second and third members 103 and 105 may be advanced together in the direction of arrow A relative to the first member 101, which is not similarly advanced.

It is further noted that in the nested assembly 100 of FIGS. 1A-1B, the members to not "capture" any of the members that are located radially-outward when the member is moved in the direction of arrow B. For example, the first or central member 101 may move freely with respect to the second and third members 103 and 105 in the direction of arrow B and may be removed from the assembly 100. Similarly, the second member 103 may move freely with respect to the third member 105 in the direction of arrow B and may also be removed from the outermost member 105 assembly 100.

Although the multi-stage dilator and cannula assembly 100 of FIGS. 1A-1B illustrates three members 101, 103 and 105 in a nested configuration, it will be understood that an assembly 100 in various embodiments may include only two nested members (e.g., members 101 and 103) or may include more than three nested members (e.g., one or more additional members may be located radially outwards from third member 105).

The embodiment of FIG. 1A-1B also includes a marker device 119 which may be used for a motion tracking/surgical navigation system, as described in further detail below. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers. A 3D model of the space may be constructed in software based on the signals detected by the sensing device.

The marker device 119 of FIGS. 1A-1B includes a set of markers 121 secured to a rigid support structure 123. The markers 121 may comprise passive markers that are configured to reflect light at particular wavelengths (e.g., IR light) or may be active markers having a light source (e.g., LED source) for generating light in a particular wavelength or wavelength range that may be sensed by a sensing device (e.g., one or more cameras) as described above. The markers 121 may be secured to the support structure 123 to provide a fixed, known geometric relationship of the markers 121 to each other and to the assembly 100, which may enable both the position (x, y, z) and the orientation (yaw, pitch, roll) of the assembly 100 to be fully resolved. The particular geometric pattern of the markers 121 may be associated with the assembly 100 in the motion tracking software, and may enable the motion tracking system to identify and track the assembly 100 in three-dimensional space. In this embodiment, the marker device 119 is secured to the c-shaped protrusion 117 of the third member 105 of the assembly 100, although it would be understood that the marker device may be secured at another position on the assembly 100. In embodiments, the support structure 123 of the marker device 119 may be integrally formed with a component of the assembly 100.

A multi-stage dilator and cannula assembly 100 such as shown in FIGS. 1A-1B may be used in surgical procedures, including minimally invasive surgical procedures, to provide tissue dilation and opening of a portal to enable the surgeon to access and provide treatment to anatomical feature of interest. FIGS. 2A-2G schematically illustrate an assembly 100 such as described above used to perform a surgical procedure. In the non-limiting embodiment of FIGS. 2A-2G, the assembly 100 is used to perform a minimally-invasive spinal surgical procedure, although it will be understood that an assembly 100 of the present disclosure is not limited to use in such procedures, and may be used in a wide variety of surgical procedures, including, without limitation, various types of orthopedic, neurological, cardiothoracic and general surgical procedures.

Figure 2A:
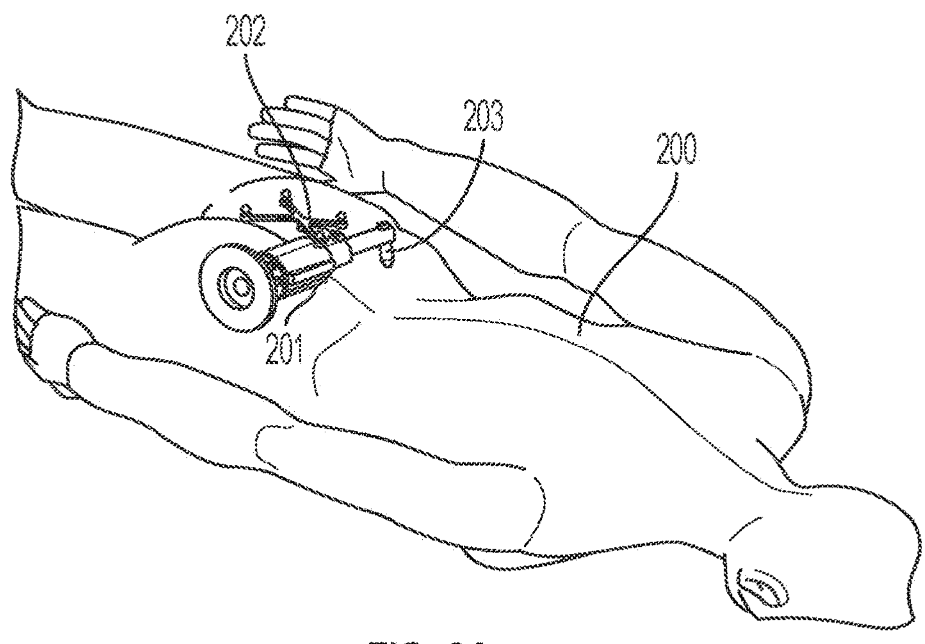
FIGS. 2A-2G schematically illustrate an embodiment dilator and cannula assembly used to perform a surgical procedure.

FIG. 2A illustrates a patient 200 supported in a prone position, such as on a surgical table (not shown for clarity). A holding mechanism 201 configured to receive a multi-stage dilator and cannula assembly 100 as described above is located above the patient 200. The holding mechanism 201 is preferably attached to a suitable support structure (not shown in FIG. 2 for clarity) that may maintain the position and orientation of the holding mechanism 201 with respect to the patient 200. In some embodiments, the support structure may be a moveable arm or boom to which the holding mechanism 201 is attached, and which may be locked in place when the holding mechanism 201 is moved to a desired position and orientation with respect to the patient 200. In some embodiments, such as described with reference to FIG. 3 below, the support structure may be a robotic arm and the holding mechanism 201 may comprise an end effector 302 attached to the end of the robotic arm 301 (see FIG. 3). The robotic arm may be controlled to move the end effector to a desired position and orientation with respect to the patient 200. The end effector/holding mechanism 201 may include a marker device 202 similar to the marker device 119 described above with reference to FIGS. 1A-1B to enable the position and/or orientation of the end effector/holding mechanism 201 to be tracked using a motion tracking system.

Figure 2B:
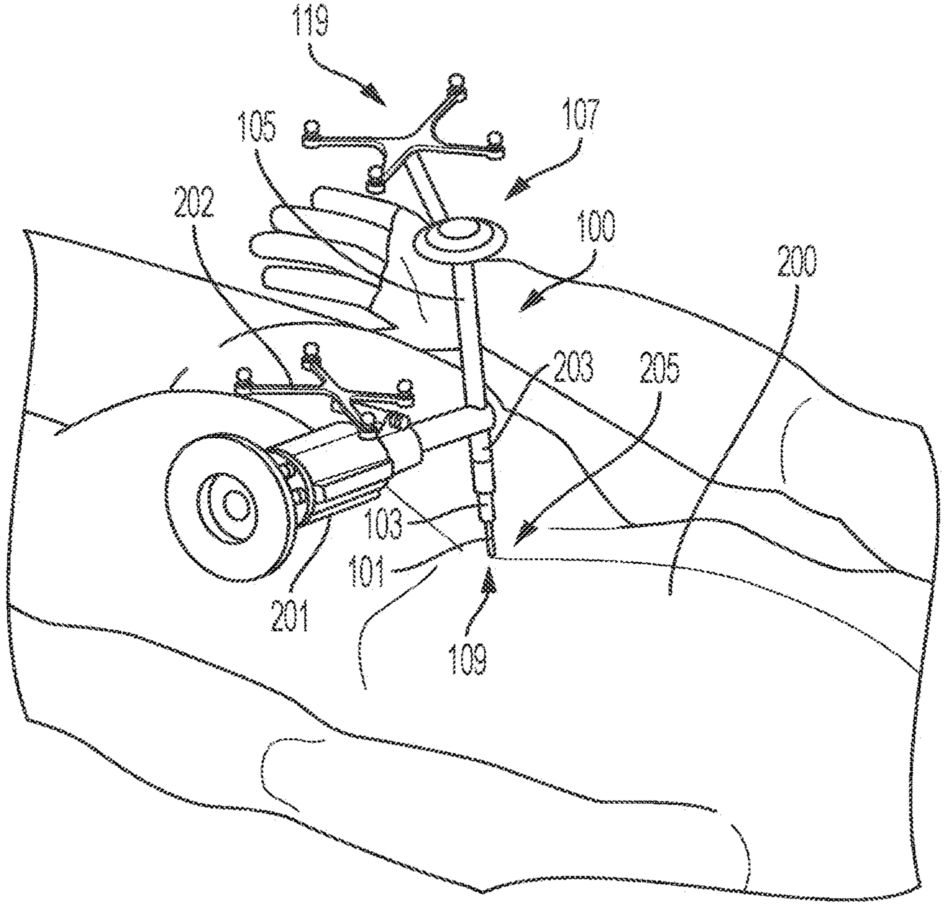

The end effector/holding mechanism 201 may include a hollow tube or cannula 203 that may be sized and shaped to receive a multi-stage dilator and cannula assembly 100 as described above. FIG. 2B illustrates the multi-stage dilator and cannula assembly 100 inserted into the hollow tube or cannula 203. The assembly 100 is configured as shown in FIG. 1A, with the head ends 107 of the nested members 101, 103, 105 positioned adjacent to one another, the tip end 109 of the first (i.e., pilot) member 101 projecting a short distance (e.g., approximately 25 mm) below the tip end 109 of the second member 103, and the tip end 109 of the second member 103 projecting a short distance (e.g., approximately 25 mm) below the tip end 109 of the third member 105.

The surgeon may then push down on the head end 107 of the first (i.e., pilot) member 101 of the assembly, causing the tip end of 109 of the first member 101 to enter a small, previously-made incision 205 in the patient's skin and create a pilot hole within the patient's body. As the first member 101 advances, the head end 107 of the first member 101 pushes down on and "captures" the second and third members 103 and 105 of the assembly, causing all three members of the assembly to advance together. As the assembly 100 advances, the tip of the second member 103 enters the patient through the incision 205. The tip end of the second member 103 follows behind the first member 101 and may partially dilate the pilot hole created by the first member 101 as the assembly 100 continues to advance into the patient, as shown in FIG. 2C.

Figure 2C:
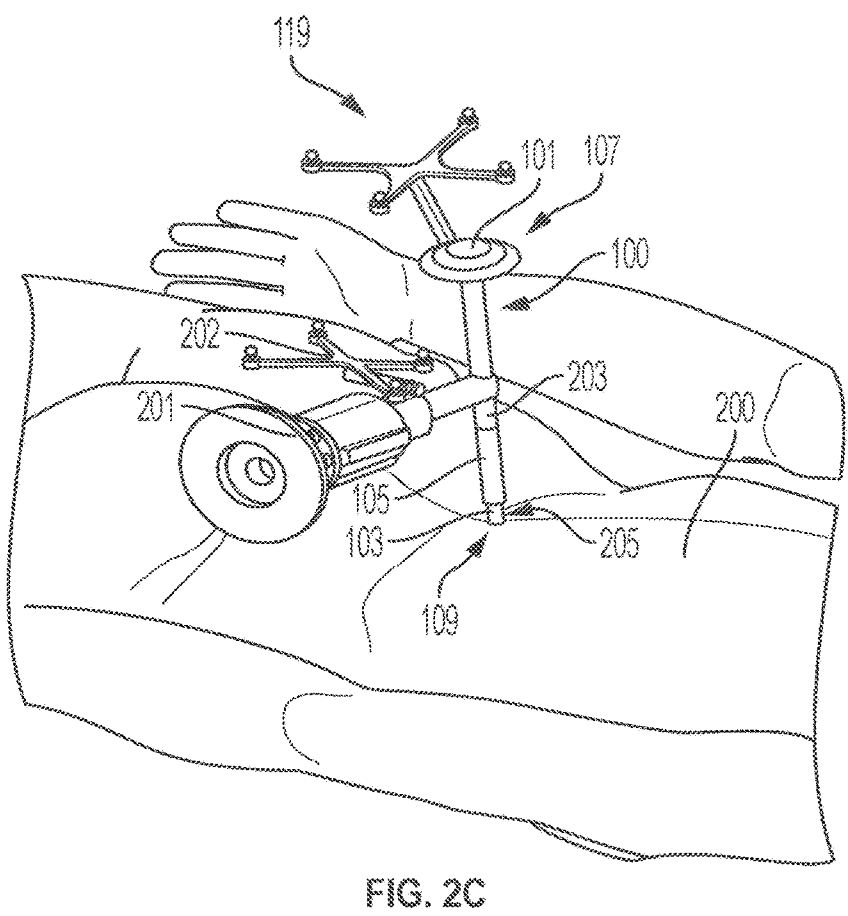

In FIG. 2C, the first (i.e., pilot) member 101 of the multi-stage dilator and cannula assembly 100 is advanced until it reaches a target position within the patient's body. The target position may be a particular portion of the patient's spine, such as a surface of a vertebral bone. In embodiments, the first member 101 may be guided to the target position using an image guided surgery system. For example, one or more diagnostic images of the patient's anatomy may be obtained pre-operatively or intra-operatively using an imaging device (e.g., an x-ray CT or fluoroscopic imaging system, an MRI system, an ultrasound imaging system, etc.). The diagnostic image(s) may be registered to the coordinate space of a motion tracking system using known surgical navigation techniques. Thus, by tracking the position and/or orientation of instruments within the surgical area, the position of the instruments relative to anatomic features in the diagnostic image(s) may be determined. For example, the marker device 119 may be used to track the motion of the multi-stage dilator and cannula assembly 100 as the first member 101 is advanced into the patient. Based on the tracked movement and known geometry of the assembly 100, the image guided surgery system may be used to determine when the tip of the first member 101 is located at a target position in the patient's body.

When the first (i.e., pilot) member 101 of the multi-stage dilator and cannula assembly 100 has reached the target position within the patient's body, the surgeon may then push down on the head end 107 of the second member 103 of the assembly, causing the second member 103 and third member 105 to continue to advance simultaneously into the patient's body while the first member 101 remains in place. The second member 103 continues to partially dilate the pilot hole, while the third member 105 provides additional dilation as the third member 105 is advanced into the patient's body.

Figure 2D:
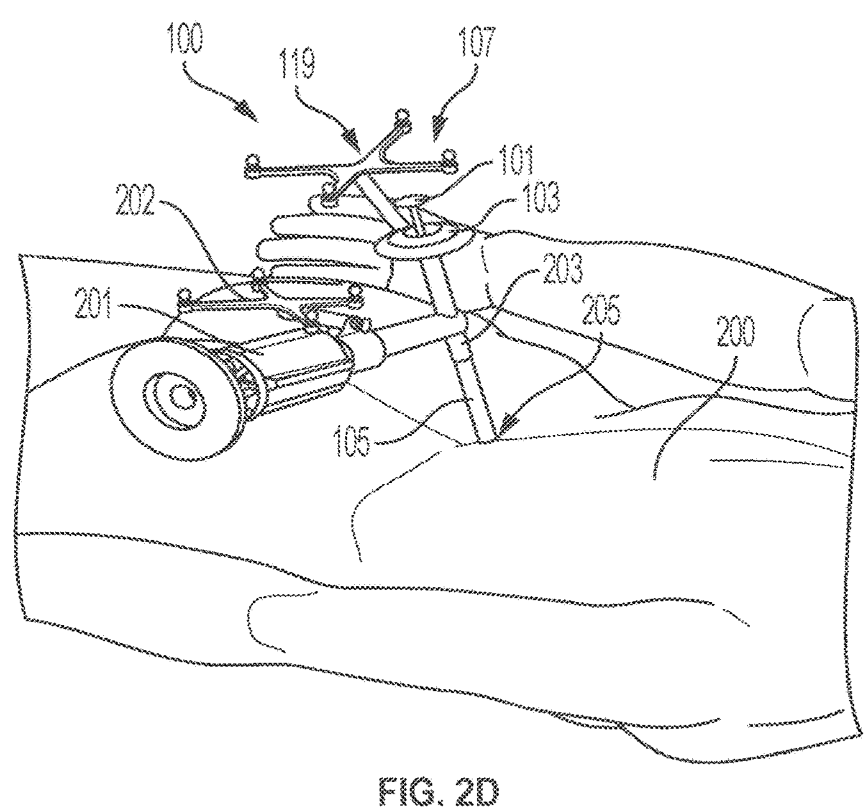

In FIG. 2D, the second member 103 of the multi-stage dilator and cannula assembly 100 is advanced until it reaches the target position within the patient's body, such that the tip ends of the first (i.e., pilot) member 101 and the second member 103 are coincident proximate to the target position. In embodiments, the second member 103 may be guided to the target position using an image guided surgery system as described above. For example, the marker device 119 may be tracked by the motion tracking system as the second and third members 103 and 105 are advanced into the patient. The image guided surgery system may be used to determine when the tip of the second member 103 is located at the target position based on the detected motion of the marker device 119 and the known geometry of the assembly 100.

The surgeon may then push down on the head end 107 of the third member 105 of the assembly, causing the third member 105 to advance further into the patient's body while the first member 101 and the second member 103 remain in place. The third member 105 may fully dilate the pilot hole as the third member 103 is advanced to the target position in the patient's body.

Figure 2E:
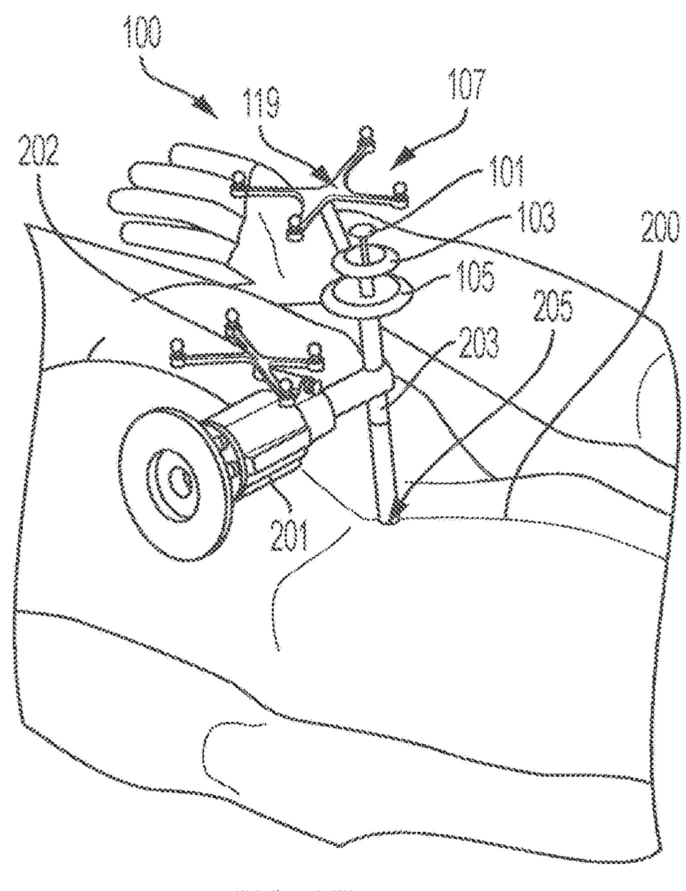

In FIG. 2E, the third member 105 of the multi-stage dilator and cannula assembly 100 is advanced until it reaches the target position within the patient's body, such that the tip ends of the first, second and third members are all coincident proximate to the target position. In embodiments, the third member 105 may be guided to the target position using an image guided surgery system as described above. For example, the marker device 119 may be tracked by the motion tracking system as the third member 105 is advanced into the patient. The image guided surgery system may be used to determine when the tip of the third member 105 is located at the target position based on the detected motion of the marker device 119 and the known geometry of the assembly 100.

Figure 2F:
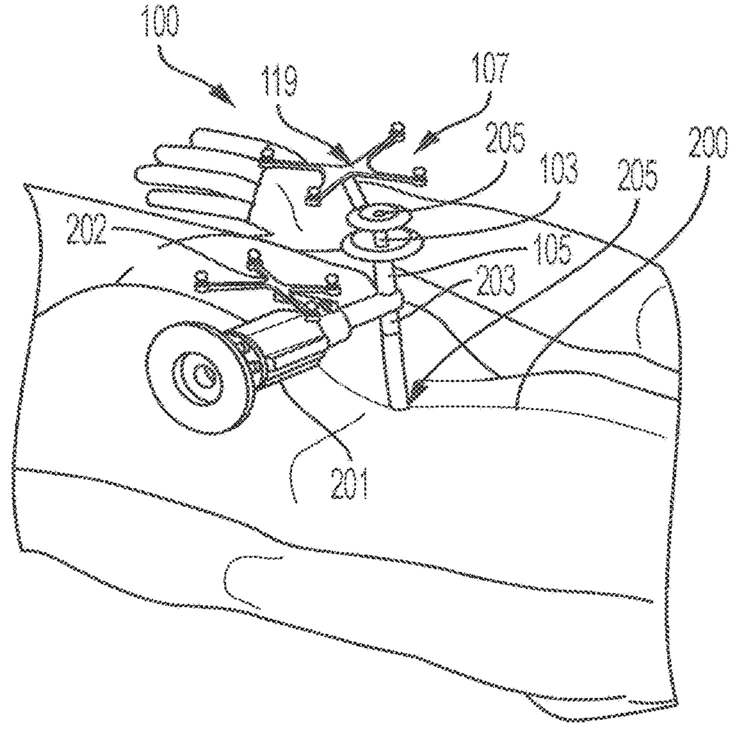

In FIG. 2F, the first (i.e., pilot) member 101 of the multi-stage dilator and cannula assembly 100 may be removed from the assembly 100 by sliding the first member 101 up and out through the opening 205 in the second member 103. The opening 205 of the second member 103 may thus provide an open portal or passageway to the target position in the patient's body. The opening 205 may be sized to enable the surgeon to insert one or more invasive surgical tools (e.g., a drill bit, a screw, a needle, a cannula, a tool for gripping or cutting, an electrode, an implant, a radiation source, a drug and an endoscope) through the opening 205 to the target position. For example, the opening 205 may be used to guide a drill bit to the surface of the patient's bone, such as a vertebral bone, where the surgeon may use the drill bit to form a pilot hole in the bone for the subsequent insertion of a screw (e.g., a pedicle screw) or other implant. In one non-limiting embodiment, the opening 205 in the second member 103 may have a diameter of approximately 4 mm (e.g., 2-5 mm). The one or more surgical tools may then be removed from the opening 205.

Figure 2G:
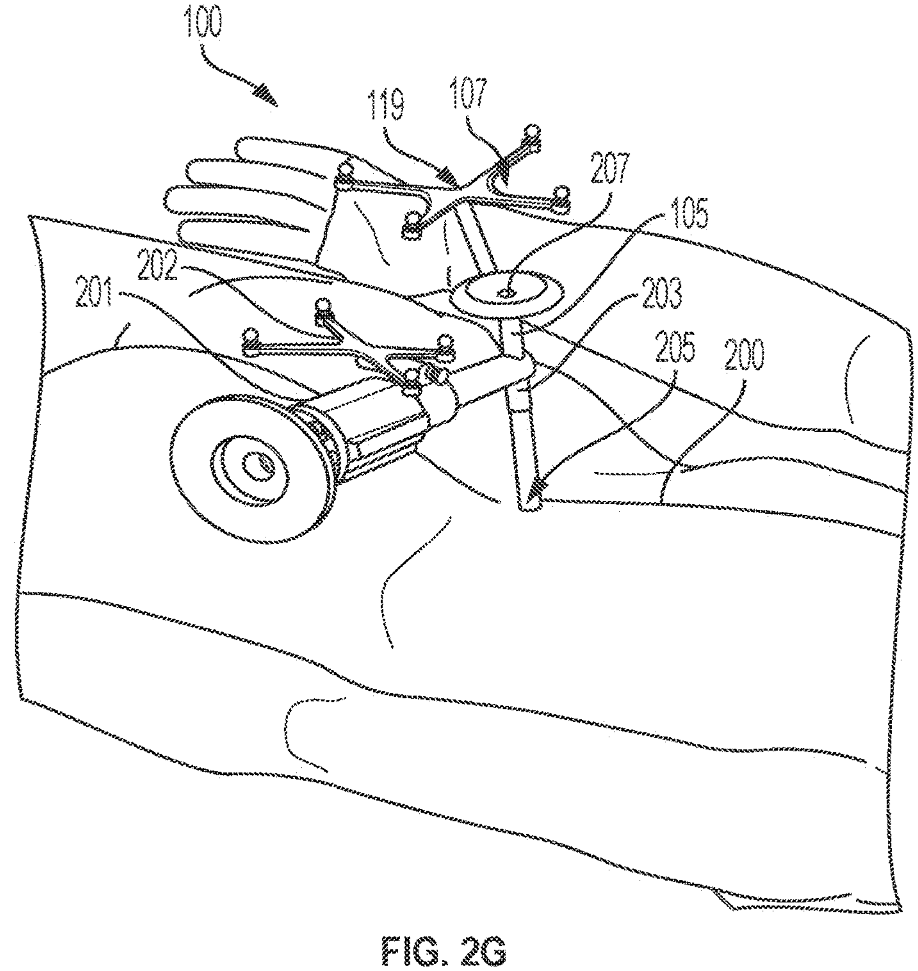

In FIG. 2G, the second member 103 of the multi-stage dilator and cannula assembly 100 may be removed from the assembly 100 by sliding the second member 103 up and out through the opening 207 in the third member 105. The opening 207 in the third member 105 may be larger than the opening 205 in the second member 103, and may thus provide an enlarged portal or passageway to the target position in the patient's body. The opening 207 may enable the surgeon to insert one or more additional surgical tools (e.g., a drill bit, a screw, a needle, a cannula, a tool for gripping or cutting, an electrode, an implant, a radiation source, a drug and an endoscope) to reach the target position. The one or more additional surgical tools inserted through opening 207 may optionally be larger than the surgical tool(s) inserted through opening 205. For example, the opening 207 may be used to guide a screw (e.g., a pedicle screw) and screw driver or another implant or tool down to the surface of the patient's bone, where the surgeon may insert the screw into the patient's bone using the previously-drilled pilot hole in the bone. In one non-limiting embodiment, the opening 207 in the second member 105 may have a diameter of approximately 9 mm (e.g., 7-10 mm). The one or more additional surgical tools may then be removed from the opening 207.

The third member 105 of the multi-stage dilator and cannula assembly 100 may then be removed from the patient's body. The assembly 100 may then be reassembled by inserting the first and second members 101, 103 into the third member 105. Optionally, the end effector/holding mechanism 201 may be moved to another location above the patient's body and the process may be repeated.

Figure 3:
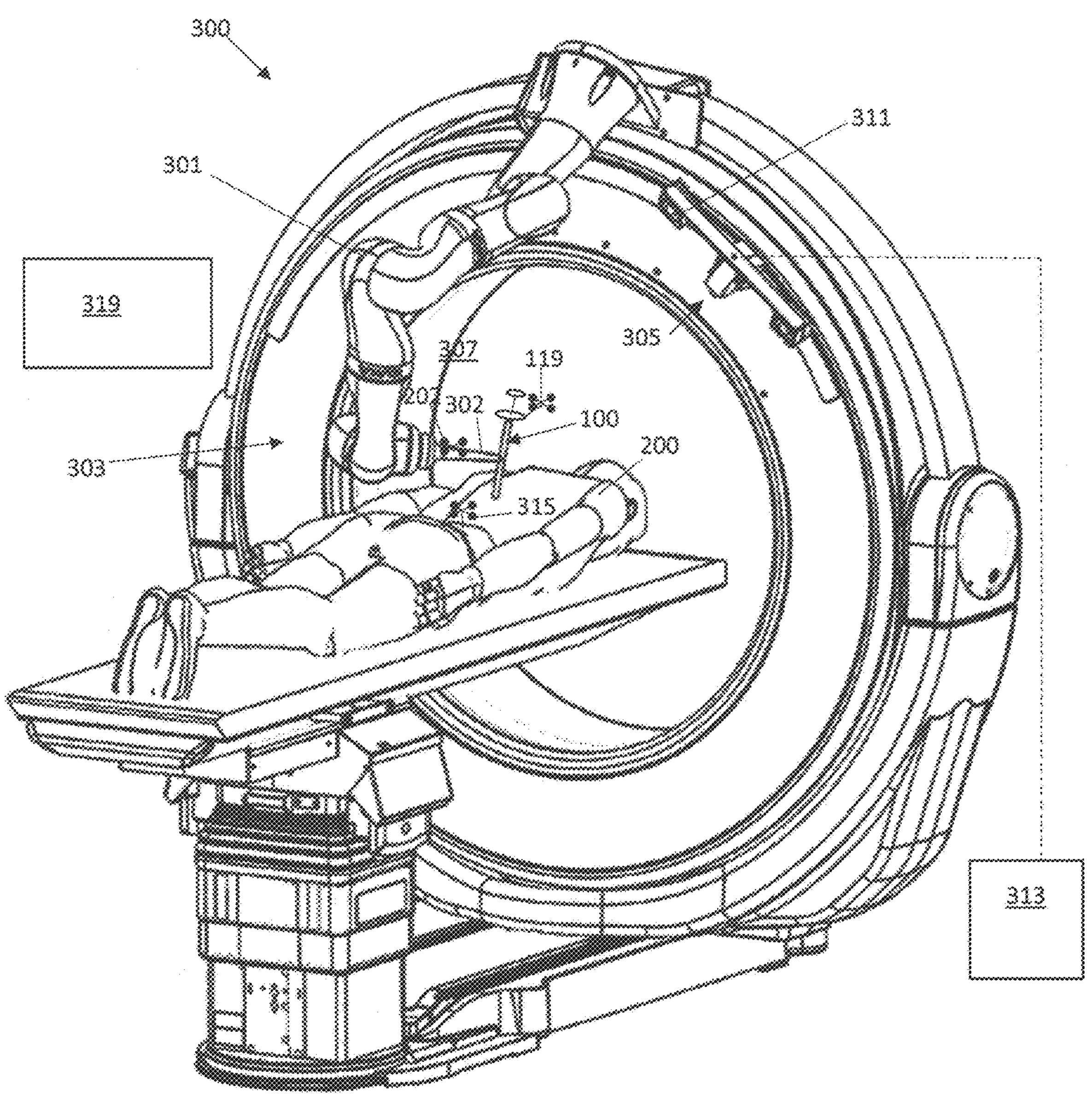
FIG. 3 illustrates a computer assisted surgical system for use with a dilator and cannula assembly according to an embodiment.

FIG. 3 illustrates a system 300 for performing robotically-assisted image-guided surgery using a multi-stage dilator and cannula assembly 100 according to various embodiments. The system 300 in this embodiment includes a robotic arm 301, an imaging device 303 and a motion tracking system 305. The robotic arm 301 may comprise a multi-joint arm that includes a plurality of linkages connected by joints having actuator(s) and optional encoder(s) to enable the linkages to bend, rotate and/or translate relative to one another in response to control signals from a robot control system. The robotic arm 301 may be fixed to a support structure at one end and may have an end effector 302 at the other end of the robotic arm 301. A multi-stage dilator and cannula assembly 100 is supported by the end effector 302, as described above with reference to FIGS. 2A-2G.

The imaging device 303 may be used to obtain diagnostic images of a patient 200, which may be a human or animal patient. In embodiments, the imaging device 303 may be an x-ray computed tomography (CT) imaging device. The patient 200 may be positioned within a central bore 307 of the imaging device 303 and an x-ray source and detector may be rotated around the bore 307 to obtain x-ray image data (e.g., raw x-ray projection data) of the patient 200. The collected image data may be processed using a suitable processor (e.g., computer) to perform a three-dimensional reconstruction of the object. In other embodiments, the imaging device 303 may comprise one or more of an x-ray fluoroscopic imaging device, a magnetic resonance (MR) imaging device, a positron emission tomography (PET) imaging device, a single-photon emission computed tomography (SPECT), or an ultrasound imaging device. In embodiments, image data may be obtained pre-operatively (i.e., prior to performing a surgical procedure) or intra-operatively (i.e., during a surgical procedure) by positioning the patient 200 within the bore 307 of the imaging device 303. In the system 300 of FIG. 3, this may be accomplished by moving the imaging device 303 over the patient 200 to perform a scan while the patient 200 may remain stationary.

The motion tracking system 305 in this embodiment includes a plurality of marker devices 119, 202 and 315 and a stereoscopic optical sensor device 311 that includes two or more cameras (e.g., IR cameras). The optical sensor device 311 may include one or more IR sources (e.g., diode ring(s)) that direct radiation (e.g., IR radiation) into the surgical field, where the radiation may be reflected by the marker devices 119, 202 and 315 and received by the cameras. A computer 313 may be coupled to the sensor device 311 and may determine the positions and orientations of the marker devices 119, 202, 315 detected by the cameras using, for example, triangulation techniques. A 3D model of the surgical space may be generated and continually updated using motion tracking software implemented by the computer 313. In embodiments, the computer 313 may also receive image data from the imaging device 303 and may register the image data to a common coordinate system with the motion tracking system 305 using image registration techniques as are known in the art. In embodiments, a reference marker device 315 (e.g., reference arc) may be rigidly attached to a landmark in the anatomical region of interest (e.g., clamped or otherwise attached to the spinous process of a patient's vertebrae) to enable the anatomical region of interest to be continually tracked by the motion tracking system 305. Another marker device 202 may be rigidly attached to the robotic arm 301, such as on the end effector 302 of the robotic arm 301, to enable the position of robotic arm 301 and end effector 302 to be tracked using the motion tracking system 305. The computer 313 may include software configured to perform a transform between the joint coordinates of the robotic arm 301 and the common coordinate system of the motion tracking system 305, which may enable the position and orientation of the end effector 302 of the robotic arm 301 to be controlled with respect to the patient 200.

The system 300 may also include a display device 319 as schematically illustrated in FIG. 3. The display device 319 may display image data of the patient's anatomy obtained by the imaging device 303. The display device 319 may facilitate planning for a surgical procedure, such as by enabling a surgeon to define one or more target positions in the patient's body and/or a path or trajectory into the patient's body for inserting surgical tool(s) to reach a target position while minimizing damage to other tissue or organs of the patient. The position and/or orientation of one or more objects tracked by the motion tracking system 305 may be shown on the display 319, and may be shown overlaying the image data. For example, the position and/or orientation of a multi-stage dilator and cannula assembly 100 with respect to the patient's anatomy may be graphically depicted on the display 319 based on the tracked position/orientation of the marker device 119 fixed to the assembly 100 and the known geometry of the assembly 100, which may be pre-registered with the motion tracking system 305.

Figure 4:
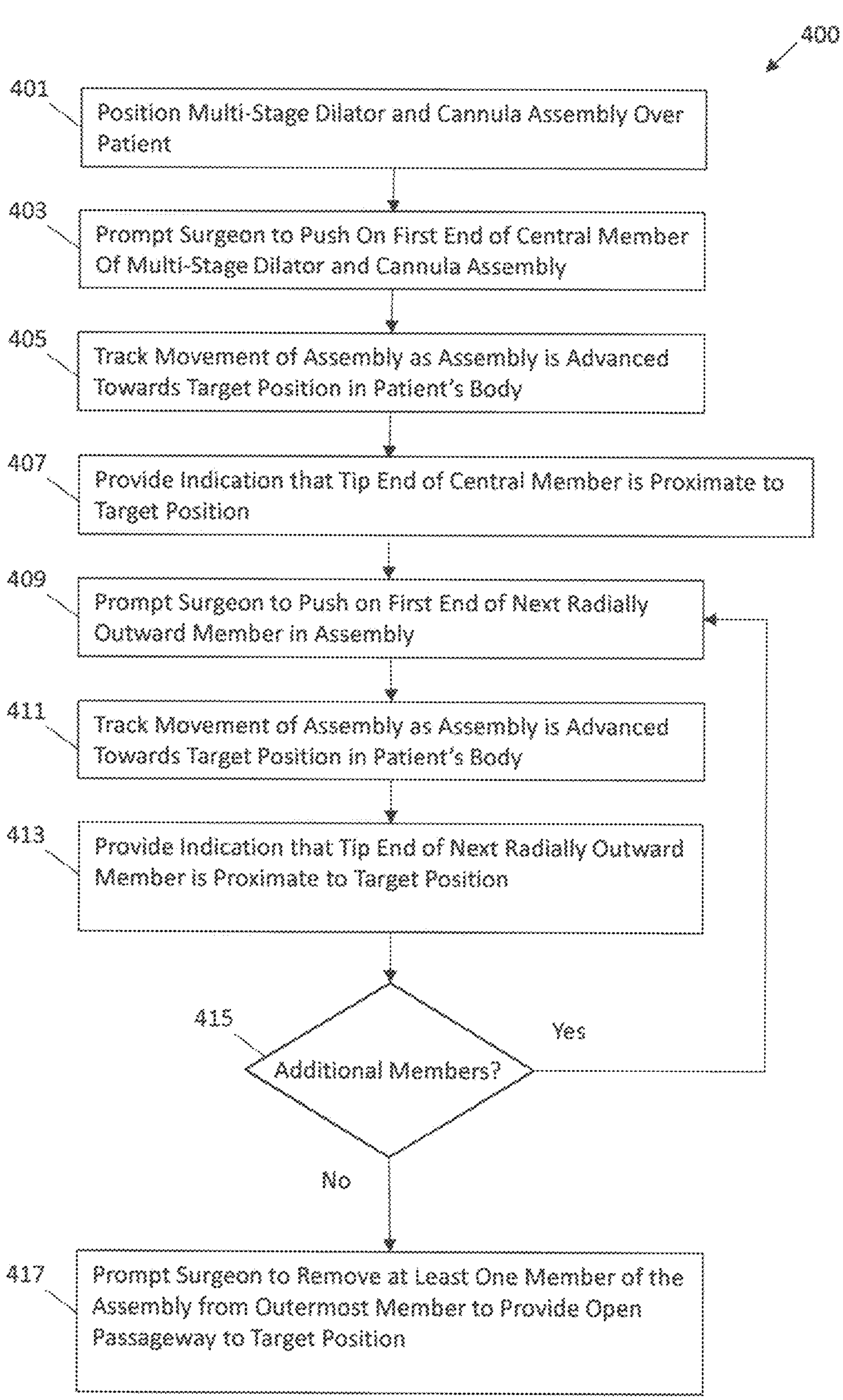
FIG. 4 is a process flow diagram illustrating a method for performing computer assisted surgery using a dilator and cannula assembly according to an embodiment.

FIG. 4 is a process flow diagram that illustrates a method 400 for performing a robotically-assisted image-guided surgical procedure using a multi-stage dilator and cannula assembly 100 according to one embodiment. The multi-stage dilator and cannula assembly 100 may include a plurality of elongated members in a nested configuration, as described above with reference to FIGS. 1A-2G. The method 400 may be performed using a system 300 as described above with reference to FIG. 3.

In step 401 of method 400, a multi-stage dilator and cannula assembly 100 may be positioned over a patient. The assembly 100 includes a plurality of elongated members in a nested configuration, including a central member and at least one additional member located radially outward of the central member. In various embodiments, the multi-stage dilator and cannula assembly 100 may be secured to an end effector of a robotic arm. The robotic arm may move the end effector to a position and orientation such that the multi-stage dilator and cannula assembly 100 may be inserted into the patient's body and advanced to a pre-determined target position in the patient's anatomy. The target position may be defined by a surgeon using image data obtained from an imaging device, as described above.

In step 403 of method 400, the surgeon may be prompted to push down on a first end of the central member of the multi-stage dilator and cannula assembly to advance the central member and at least one additional member located radially outward of the central member towards the pre-determined target position. The surgeon may be prompted via instructions provided on a display device, such as the display device 319 illustrated in FIG. 3, and/or by another perceptible means, such as by an audible instruction.

In step 405, the movement of the multi-stage dilator and cannula assembly may be tracked using a motion tracking system as the assembly is advanced towards the pre-determined target position. In step 407, an indication that the tip end of the central member of the assembly is proximate to (e.g., within 3 mm of, such as within about 1 mm of) the pre-determined target position may be provided.

In step 409, the surgeon may be prompted to push down on the next (i.e., adjacent) member of the assembly that is located radially outward from the central member. In step 411, the movement of the assembly may be tracked and in step 413, an indication that the tip end of the next member is proximate to the pre-determined target position may be provided.

In response to determining that there is at least one additional member in the assembly (i.e., determination block 415="Yes"), then steps 409 through 413 may be repeated for each member of the nested assembly until the tip end of the outermost member of the assembly is advanced proximate to the pre-determined target position.

In response to determining that there are no additional members of the assembly (i.e., determination block 415="No"), then in step 417 at least one member of the assembly may be removed from the outermost member to provide an open passageway to the pre-determined target position.

In various embodiments, the nested members of the multi-stage dilator and cannula assembly may be advanced to the target position in a simple and virtually continuous motion. As the assembly is advanced, it may provide progressive dilation of an opening in the patient's tissue to a desired target depth. The various members may then be selectively removed from the assembly to provide open passageways or cannula openings having different dimensions (e.g., diameters) for performing various steps of a surgical procedure. Following the surgical procedure, the outermost member of the assembly may be removed. The robotic arm may optionally move the end effector and the multi-stage dilator and cannula assembly to another location over the patient to perform a subsequent surgical procedure.

FIGS. 5A-5G schematically illustrate a method and system for performing a robot-assisted surgical procedure. The surgical procedure may be a spinal surgical procedure, such as a surgical procedure performed on the cervical spine (e.g., vertebrae C1-C7). The surgical procedure may be a minimally-invasive percutaneous surgical procedure, such as a minimally invasive cervical posterior fusion. It will be understood that other types of surgical procedures, such as thoracic or lumbar spinal procedures, could be performed using the systems and methods of the various embodiments.

Figure 5A:
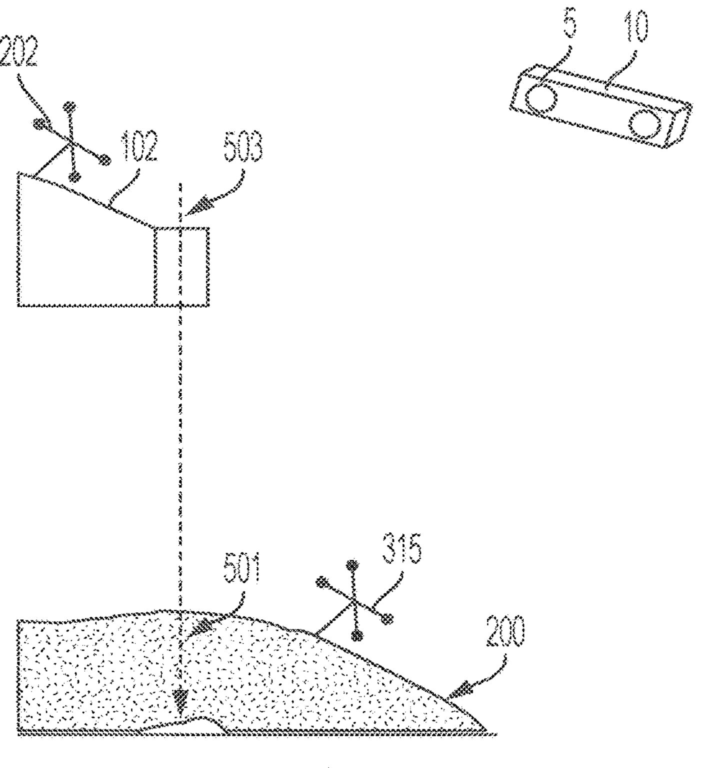
FIGS. 5A-5G schematically illustrate a method for performing robot-assisted minimally-invasive spine surgery according to an embodiment.

FIG. 5A illustrates an end effector 102 of a robotic arm (not illustrated) positioned over a pre-determined target trajectory 501. The end effector 102 may include a marker device 202 that enables the end effector 102 to be tracked using a motion tracking system 105 as described above. Another tracking device 115 may be fixed to the patient 200.

For example, tracking device 115 may be attached to a bone of the patient proximate to the surgical area, such as by clamping the tracking device 115 to the spinous process of a nearby vertebral level. Additional marker devices may be fixed to various tools used during the surgical procedure, as described further below. Each of the tools and their corresponding marker devices may be pre-registered and calibrated within a surgical navigation/image guided surgery system. Alternately or in addition, tools may be registered and calibrated by the navigation/image guided surgery system during the course of a surgical procedure. By continuously tracking the end effector 102, surgical tools and patient marker device 115 using the motion tracking system 105, each of the tracked objects may be located in three-dimensional space within a common coordinate system. In embodiments, the common coordinate system may have an origin or zero point that may be considered to be fixed relative to the surgically-relevant portion of the patient's anatomy (e.g., based on the tracked position/orientation of patient marker device 115), and may also be referred to the patient coordinate system.

The end effector 102 may include a tool holder portion 503 (e.g., a hollow tube) that is configured to hold a tool. The trajectory 501 may be defined by the surgeon during surgical planning based on pre-operative patient images (e.g., x-ray CT or fluoroscopic images, MR images, etc.). The patient images and the pre-defined trajectory may be registered or synced within the same coordinate system (e.g., the patient coordinate system) as the end effector 102 of the robotic arm. The robotic arm may be controlled to move the end effector 102 such that the central axis of the tool holder portion 503 of the end effector 102 is aligned with the defined trajectory 501 as shown in FIG. 5A. Alternately, a target location may be defined based on the patient images and the end effector 102 may be moved such that the central axis of the tool holder portion 503 intersects the target location. The robotic arm may be controlled so as to hold the trajectory defined by the end effector during a portion of the surgical procedure, such as the insertion of a surgical implant (e.g., a pedicle screw) in a target location in the patient's anatomy.

The surgeon may make a small incision through the skin of the patient overlaying the target location.

Figure 5B:
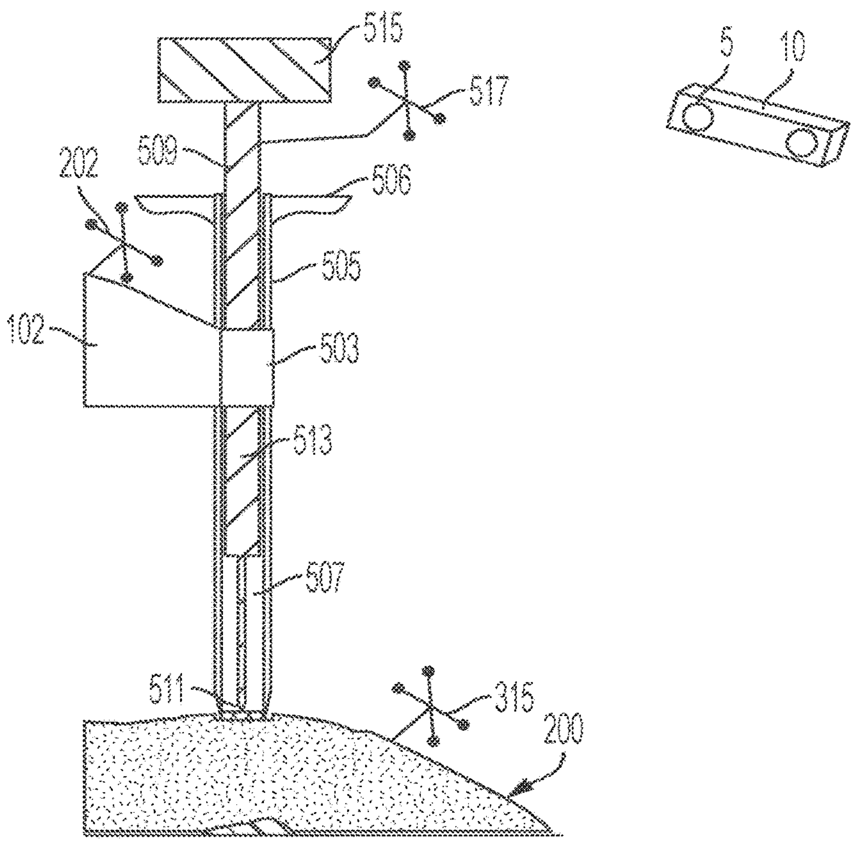

As shown in FIG. 5B, a dilator 505 may be provided within the tool holder portion 503 of the end effector 102. The dilator 505 have an outer diameter that substantially corresponds with the inner diameter of the tool holder portion 503. The dilator 505 may be slidable within the tool holder portion 503. The dilator 505 may include an opening 507 extending lengthwise through the dilator 505 as shown in FIG. 5B. The opening 507 may be configured to receive one or more tools, such as tool 509 shown in FIG. 5B.

In some embodiments, the dilator 505 may be a multi-stage dilator and cannula assembly 100 including a plurality of nested members, as described above with reference to FIGS. 1A-2G. Alternately, the dilator 505 may comprise a single member as shown in FIG. 5B. The dilator 505 may include a handle portion 506 to enable the dilator to be grasped and manipulated by a surgeon. The dilator 505 may optionally include a marker device (not shown for clarity) to enable the dilator 505 to be tracked using the motion tracking system 105.

Also shown in FIG. 5B is a tool 509 inserted through the opening 507 in the dilator 505. The tool 509 may be an awl or similar device (e.g., a needle) having a narrow pointed tip end 511, a relatively wider collar portion 513, and a handle 515. The collar portion 513 may have an outer diameter that substantially corresponds with the diameter of the opening 507 of the dilator 505. The tool 509 may be slidable within the dilator 505. The tool 509 may also include a marker device 517 fixed to the tool 509 to enable the tool 509 to be tracked using the motion tracking system 105. The tool 509 may be registered and calibrated within the surgical navigation/image guided surgery system such that the position and/or orientation of the tip end 511 of the tool 509 may be known within the patient coordinate system based on the tracked position and/or orientation of the marker device 517.

Figure 5C:
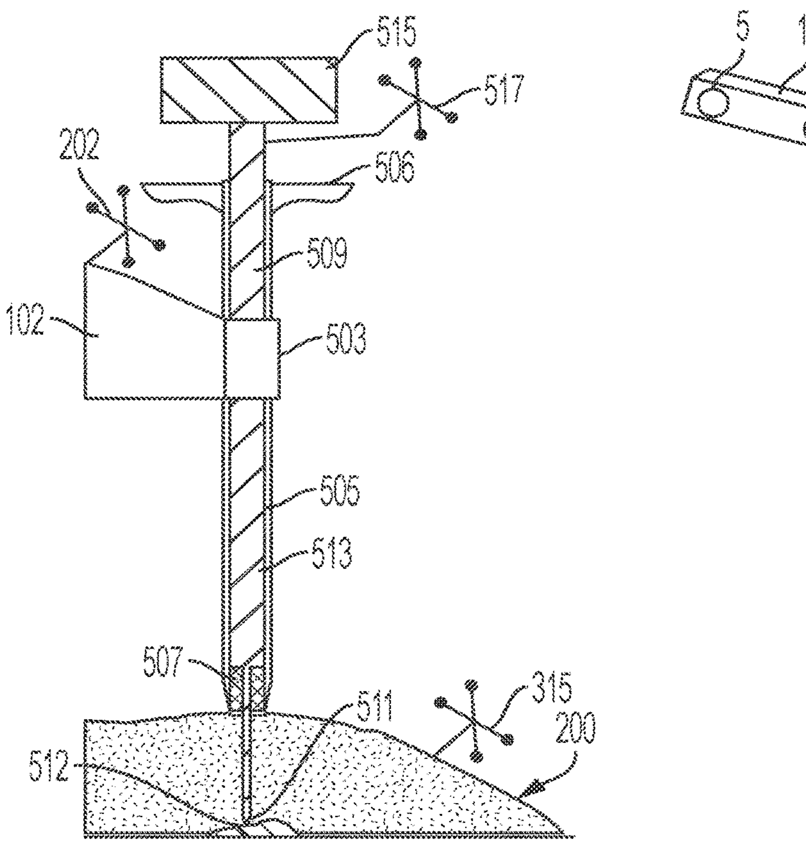

In FIG. 5C, the surgeon may push down on the handle 515 of the tool 509 to advance the tip end 511 of the tool 509 through the incision in the patient's skin and into the patient's body. The end effector 102 and cannula 505 may guide the movement of the tool 509 as the collar portion 513 slides within the opening 507 of the cannula 505 such that the tip end 511 of the tool 509 advances along the trajectory to the target position within the patient. In embodiments, the surgeon may be prompted to push down on the tool 509 via instructions provided on a display device, such as the display device 319 illustrated in FIG. 3, and/or by another perceptible means, such as by an audible instruction. The movement of the tool 509 may be tracked by the motion tracking system 105 as the tip end 511 is advanced towards the pre-determined target position. An indication that the tip end 511 of the tool is proximate to (e.g., within 3 mm of, such as within about 1 mm of) the pre-determined target position may also be provided.

FIG. 5C illustrates the tool 509 pushed down such that the tip end 511 contacts a bone 512 surface of the patient 200. In some embodiments, the surgeon may continue to push down on the tool 509 such that the tip end 511 may break the cortical surface and create a preliminary pilot hole in the bone 512. Alternately, the surgeon may remove the tool 509 from the dilator 505 and may use another tool (e.g., a Jamshidi needle) for this purpose.

Alternately, the tool 509 having a pointed tip end 511 may be integrated with a multi-stage dilator and cannula assembly 100, such as described above with reference to FIGS. 1A-2G. In various embodiments, the first (i.e., pilot) member 101 of the multi-stage dilator and cannula assembly 100 may have a narrow pointed tip end 511, as with the tool 509 shown in FIG. 5B. Pushing down on the on the pilot member 101 may cause the pointed tip end 511 to advance into the patient while also capturing and advancing one or more outer stages of the dilator into the patient, as described above. In embodiments, the integrated tool and dilator assembly may be calibrated and registered with the image guided surgery system, such that the position of the tip end 511 of the tool 509 may be known based on the tracked position of a marker fixed to the dilator assembly.

Figure 5D:
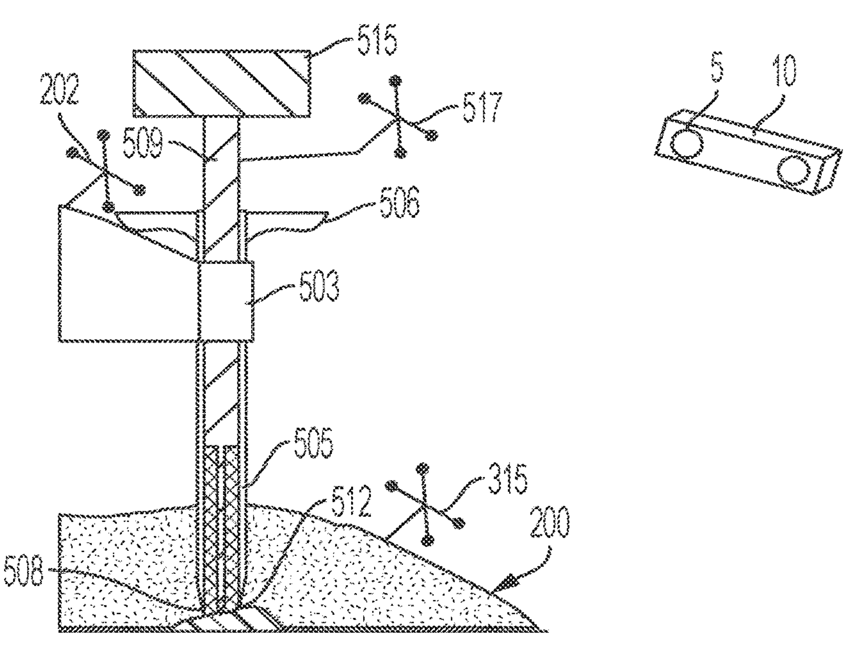

In FIG. 5D, the dilator 505 may be pushed down relative to the end effector 102 to advance the dilator 505 into the patient 200 and to dilate the opening previously made by one or more other tools (e.g., tool 509). As shown in FIG. 5D, the dilator 505 may be pushed down over the tool 509. Alternately, the tool 509 may be removed from the dilator 505 before the dilator 505 is pushed down. The dilator 505 may be advanced into the patient 200 until the tip end 508 of the dilator 505 docks against the bone 512 surface, as shown in FIG. 5D. In some embodiments, the tip end 508 of the dilator 505 may be angled or contoured to facilitate mating with the bone 512. In embodiments, the tip end 508 may include cleats or other features to dig into and/or grip the bone surface.

In embodiments, the surgeon may be prompted to push down on the dilator 505 via instructions provided on a display device, such as the display device 319 illustrated in FIG. 3, and/or by another perceptible means, such as by an audible instruction. In embodiments where the dilator 505 is tracked, the movement of the dilator 505 may be tracked by the motion tracking system 105 and displayed on a display device as the dilator 505 is advanced towards the bone 512. For a multi-stage dilator, each nested cannula may be advanced to the bone 512 to provide progressive dilation of the surgical opening.

When the dilator 505 is docked against the bone 512, the tool 509 (e.g., an awl) may be removed from the dilator 505, leaving the opening 507 in the dilator 505 providing a port to the surface of the bone 512. For a multi-stage dilator, one or more inner stages of the dilator may be removed to leave the dilator with an opening having a desired inner diameter. In embodiments of a multi-stage dilator, the inner diameter of each nested cannula may correspond with the outer diameter of particular tools and/or implants that are intended to be inserted through the cannula during the surgical procedure.

Figure 5E:
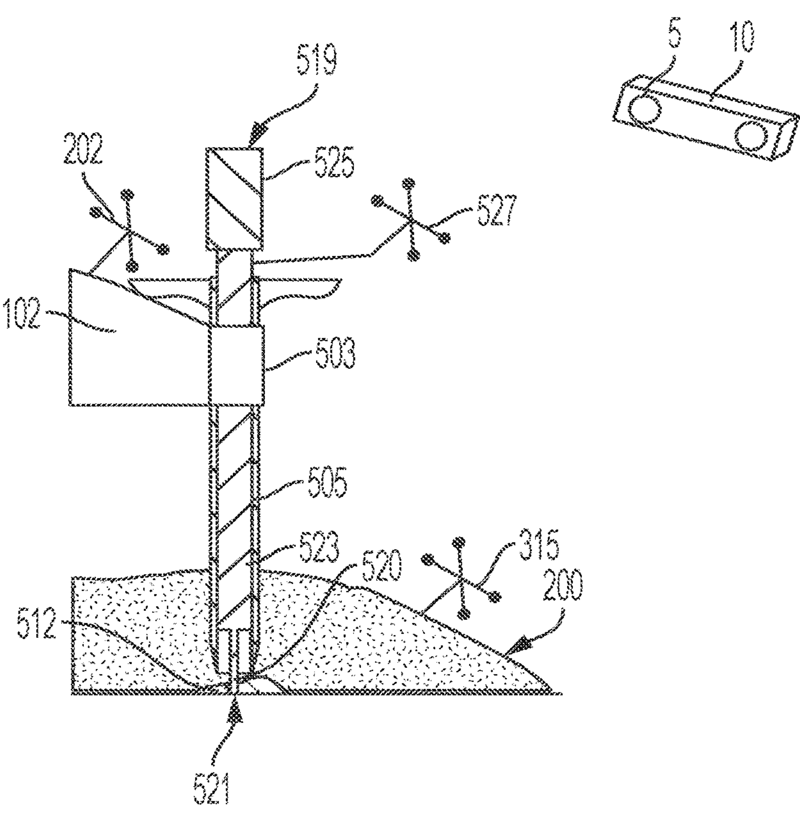

In FIG. 5E, a drill 519 is shown inserted through the opening 507 in the dilator 505. The drill 519 may include a drill bit 520 at a tip end 521 of the drill, a collar portion 523, and a handle 555. The collar portion 523 may have an outer diameter that substantially corresponds with the diameter of the opening 507 of the dilator 505. The drill 519 may also include a marker device 527 fixed to the drill 519 to enable the drill 519 to be tracked using the motion tracking system 105. The drill 519 may be registered and calibrated within the surgical navigation/image guided surgery system such that the position and/or orientation of the tip end 521 of the drill 519 may be known within the patient coordinate system based on the tracked position and/or orientation of the marker device 527.

The drill 519 may be used to create a pilot hole within the bone 512 for a surgical implant (e.g., a screw). The depth of the pilot hole may be tracked by the motion tracking system 105 (i.e., based on the position of the tip end 521 of the drill 519) and an indication of the depth may be provided on the display device 319. In some embodiments, the surgeon may be instructed to insert the drill 519 into the dilator 505 and may be prompted to use the drill 519 to create a pilot hole via instructions provided on the display device 519, and/or by another perceptible means, such as by an audible instruction. An indication that the pilot hole has reached a predetermined depth may also be provided. After the pilot hole is created, the drill 519 may be removed from the dilator 505.

Figure 5F:
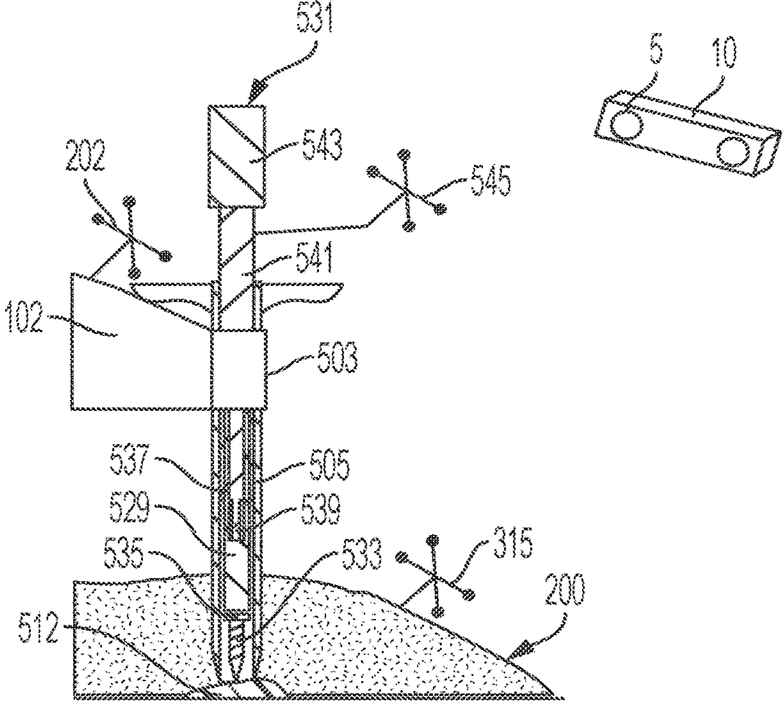

In FIG. 5F, a screw 529 and screw driver 531 are shown inserted through the opening 507 in the dilator 505. The screw 529 may include a threaded tip end 533 extending from a screw head 535, and a tab portion 537 extending from the screw head 535 opposite the threaded tip end 533. At least one of the tab portion 537 and the screw head 535 may include an outer diameter that substantially corresponds with the diameter of the opening 507 of the dilator 505. This may enable the threaded tip end 533 of the screw 529 to align with a pilot hole created by a drill 519 as shown in FIG. 5E. The screw driver 531 may include a tip end 539 that is sized and shaped to engage with a corresponding portion of the screw 529 so as to enable the screw driver 531 to apply a torque to the screw 529. The screw driver 531 may include features to enable the screw driver 531 to mate with the tab portion 537 of the screw 529 and may also include a collar 541 having an outer diameter that substantially corresponds with the diameter of the opening 507 of the dilator 505.

The screw driver 531 may also include handle 543 to enable the screw driver 531 to be gripped and manipulated (e.g., rotated) by a surgeon. A marker device 545 may be fixed to the screw driver 531 to enable the screw driver 531 to be tracked using the motion tracking system 105. In some embodiments, the screw driver 531 may be registered and calibrated within the surgical navigation/image guided surgery system such that the position and/or orientation of the tip of the screw driver 531 may be known within the patient coordinate system based on the tracked position and/or orientation of the marker device 545. The offset distance between the tip of the screw driver 531 and the tip end of the screw 529 when the screw driver 531 engages the screw 529 may also be calibrated to enable the depth of the screw within the patient's bone 512 to be determined. A graphical depiction of the screw 529 and its position within the patient may be shown overlaying the patient images on the display device 319.

The screw driver 531 may be used to insert the screw 529 within the bone 512. The depth of the insertion may be tracked by the motion tracking system 105 (i.e., based on the position of the tip of the screw driver 531 and/or the rotational displacement of the screw driver 531 as the screw driver 531 screws the screw 529 into the bone 512). An indication of the depth of screw insertion may be provided on the display device 319. In some embodiments, the surgeon may be instructed to insert the screw 529 and screw driver 531 into the dilator 505 and may be prompted to use the screw driver 531 to insert the screw 529 via instructions provided on the display device 319, and/or by another perceptible means, such as by an audible instruction. An indication that the screw 529 has been inserted to a predetermined depth may also be provided.

Figure 5G:
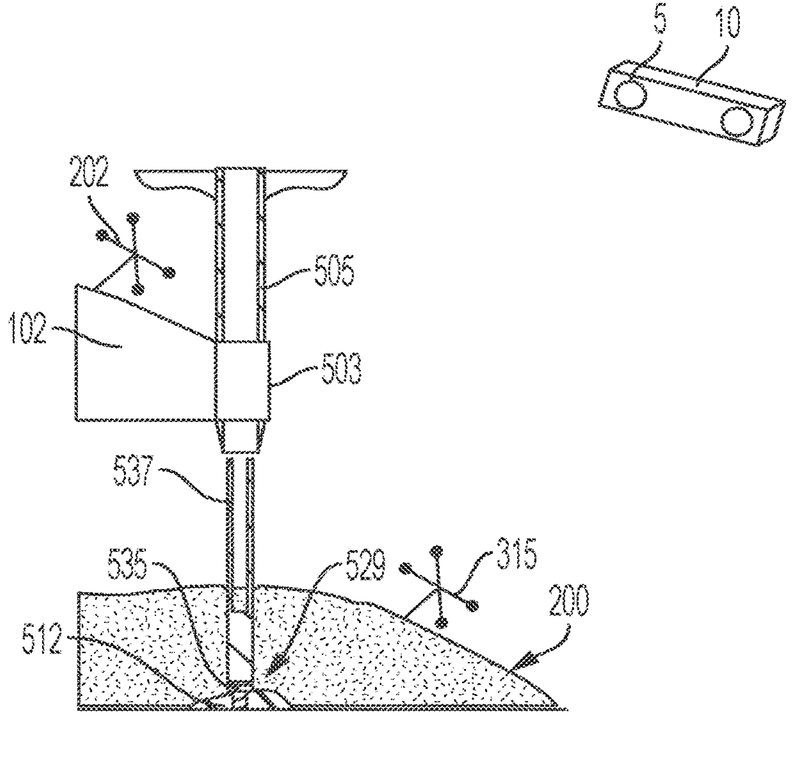

After the screw 529 has been inserted into the bone 512, the screw driver 531 may be removed from the dilator 505. The dilator 505 may then be slid upwards within the end effector 102 over the screw 529 and out of the patient 200, as shown in FIG. 5G. The screw 529 may remain fixed to the bone 512, with a portion of the tab portion 537 extending outside of the patient 200.

After a screw 529 has been placed in the patient 200, the robotic arm may optionally move the end effector 102 to a next target position/trajectory over the patient 200, and the above-described process may be repeated for the insertion of another screw 529.

In embodiments, the positions of each screw 529 within the patient coordinate system may be saved within the surgical navigation/image guided surgery system, which may facilitate rod placement, including the curvature and/or insertion pathway for one or more rods. In embodiments, the tab portions 537 of the screws 529 may be used to secure the rods (such as by inserting and/or tightening a set screw or other fastening mechanism against a rod through the tab portions 537). The tab portions 537 may then be removed (e.g., using tab breakers), leaving the rest of the screw 529 in place.

Figure 6:
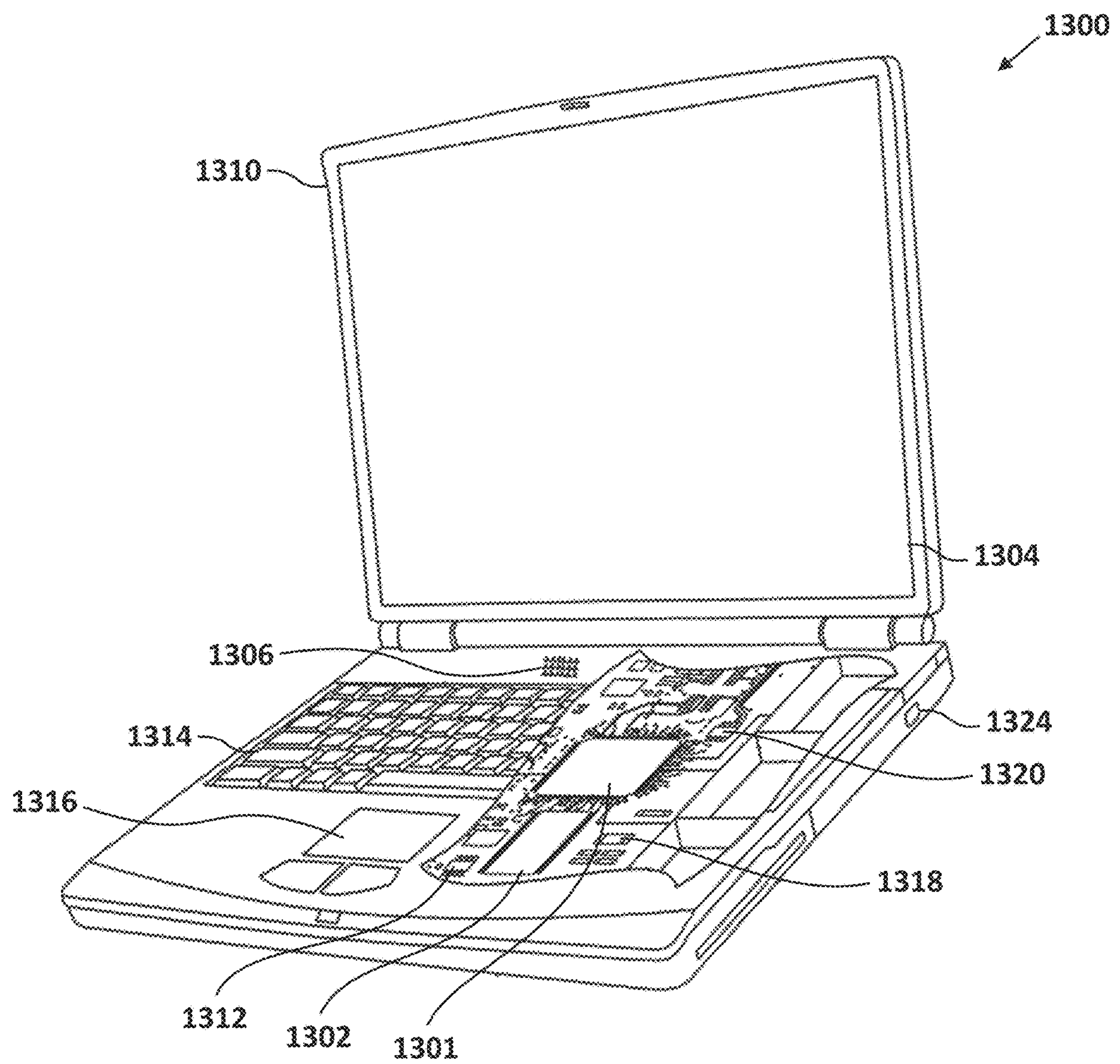
FIG. 6 schematically illustrates a computing device which may be used for performing various embodiments.

FIG. 6 is a system block diagram of a computing device useful to perform functions of a processing control unit, such as computer 313 described above with reference to FIG. 3. While the computing device 1300 is illustrated as a laptop computer, a computing device providing the functional capabilities of the computer device 1300 may be implemented as a workstation computer, an embedded computer, a server computer, a desktop computer or a handheld computer (e.g., tablet, a smartphone, etc.). A typical computing device 1300 may include a processor 1301 coupled to an electronic display 1304, a speaker 1306 and a memory 1302, which may be a volatile memory as well as a nonvolatile memory (e.g., a disk drive). When implemented as a laptop computer or desktop computer, the computing device 1300 may also include a floppy disc drive, compact disc (CD) or DVD disc drive coupled to the processor 1301. The computing device 1300 may include an antenna 1310, a multimedia receiver 1312, a transceiver 1318 and/or communications circuitry coupled to the processor 1301 for sending and receiving electromagnetic radiation, connecting to a wireless data link, and receiving data. Additionally, the computing device 1300 may include network access ports 1324 coupled to the processor 1301 for establishing data connections with a network (e.g., LAN coupled to a service provider network, etc.). A laptop, desktop or workstation computer 1300 typically also includes a keyboard 1314 and a mouse pad 1316 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A system for performing robotically-assisted image guided surgery comprising:

a motion tracking system operable to track one or more objects in a surgical area; and a robotic arm; and a dilator assembly comprising a first elongated member and a second elongated member, each of the first elongated member and the second elongated member include a longitudinal axis, the first elongated member including a first projection extending transverse to the longitudinal axis at a head end of the first elongated member, and the second elongated member including a second projection extending transverse to the longitudinal axis at a head end of the second elongated member, the first elongated member is configured to be received by the second elongated member in a nested arrangement, and the first projection of the first elongated member abuts and is restrained from axial movement in one direction by the second projection of the second elongated member when the first elongated member is advanced relative to the second elongated member in a first direction, the first elongated member is slidable relative to the second elongated member;

wherein the robotic arm is configured to hold and move the dilator assembly to one or more predetermined positions over a body of a patient using tracking data from the motion tracking system; and wherein the first elongated member is connected with a tracking device, the tracking device configured to be tracked by the motion tracking system.

2. The system of claim 1, further comprising a third elongated member, the third elongated member including a shaft and a handle, the shaft configured to form a hole in a patient when advanced through the first elongated member and the second elongated member.

3. The system of claim 2, wherein the second elongated member includes a protrusion that is shaped to receive the handle of the third elongated member.

4. The system of claim 2, wherein a portion of the third elongated member is dimensioned larger than an opening of the first elongated member and wherein movement in a first direction of the third elongated member causes the portion of the third elongated member that is dimensioned larger than the opening of the first elongated member to push down on the first elongated member.

5. The system of claim 2, wherein the third elongated member includes another tracking device configured to be tracked by the motion tracking system.

6. The system of claim 2, wherein the third elongated member is a screw driver.

7. The system of claim 2, wherein the third elongated member is a drill.

8. The system of claim 2, wherein the third elongated member is configured to be removed and replaced with a fourth elongated member, wherein the third elongated member is a first tool, and the fourth elongated member is a second tool.

9. The system of claim 8, wherein the third elongated member at least one of an awl, a dilator, a cannula, a drill, a screw driver, and a needle.

10. The system of claim 8, wherein the first tool is different than the second tool.

11. The system of claim 1, wherein the robotic arm includes an arm tracking device configured to be tracked by the motion tracking system.

12. The system of claim 1, wherein the first projection of the first elongated member is dimensioned larger than an opening of the second elongated member and wherein movement in a first direction of the first elongated member causes the first projection to push down on the second elongated member.

13. The system of claim 1, wherein the second elongated member is an end effector connected to the robotic arm.

14. The system of claim 1, further comprising a patient tracking device connected with the patient, the patient tracking device configured to be tracked by the motion tracking system; and wherein the patient tracking device and tracking device of the first elongated member are located in three-dimensional space within a common coordinate system.

15. The system of claim 14, further comprising patient images that are registered with the motion tracking system, the patient images are used to determine a predefined target trajectory;

wherein the target trajectory is registered with the common coordinate system, and the robotic arm is configured to move the dilator assembly to the target trajectory.

* * * * *